US00PP10929P

United States Patent [19]

Zary

[11] Patent Number: Plant 10,929

[45] Date of Patent: Jun. 1, 1999

[54] MINIATURE ROSE PLANT NAMED 'JACPOLY'

[75] Inventor: Keith W. Zary, Thousand Oaks, Calif.

[73] Assignee: Bear Creek Gardens, Inc., Medford, Oreg.

[21] Appl. No.: 09/000,603

[22] Filed: Dec. 30, 1997

[51] Int. Cl.[6] ..... A01H 5/00

[52] U.S. Cl. ..... Plt./128

[58] Field of Search ..... Plt./128, 121

*Primary Examiner*—Howard J. Locker

*Attorney, Agent, or Firm*—Klarquist Sparkman Campbell Leigh & Whinston, LLP

[57] ABSTRACT

Miniature rose plant having a compact, upright, well-branched growth habit; a resistance to rust and powdery mildew; very glossy, small, dark green foliage; and very attractive, well-formed, small, pure pink flowers.

1 Drawing Sheet

The present invention relates to a new and distinct variety of rose plant of the miniature class which was originated by me by crossing the variety 'JACship', (U.S. Plant Pat. No. 7,948), with the variety 'JACdew', (U.S. Plant Pat. No. 5,122).

The primary objective of this breeding was to produce a new rose variety having the small, dark green foliage, good flower form, vigorous growth, and well-branched habit of the female parent combined with the resistance to disease of the male parent. The objective was substantially achieved, along with other desirable improvements, as evidenced by the following unique combination of characteristics that are outstanding in the new variety and that distinguish it from its parents, as well as from all other varieties of which I am aware:

1. Attractive, well formed, pure pink flowers;
2. Glossy, small, dark green foliage;
3. Upright, compact, well-branched habit of growth;
4. Resistance to powdery mildew and rust.

Asexual reproduction of this new variety by softwood cuttings, as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JACship (U.S. Plant Pat. No. 7,948).

*Pollen parent.*—JACdew (U.S. Plant Pat. No. 5,122).

Classification:

*Botanical.*—Rosa hybrida.

*Commercial.*—Miniature.

FLOWER

Observations made from specimens grown in a garden environment at Somis, Calif. from January, 1996–September, 1997.

Blooming habit: Continuous.

Bud:

*Size.*—One-half inch long when the petals start to unfurl.

*Form.*—The bud form is long, pointed ovoid.

*Color.*—When sepals first divide, bud color is Red group 49A; When half blown, the upper sides of the petals are Red group 49B; and the lower sides of the petals are Red group 49B.

*Sepals.*—Color: Green group 138A and bronzy when exposed to the sun. Surface texture: Covered with fine hairs. There are three normally appendaged sepals. There are two unappendaged sepals with hairy edges.

*Receptacle.*—Color: Green group 137B. Shape: Funnel. Size: Small (¼" long×3/16" wide). Surface: Smooth.

*Peduncle.*—Length: Short (1¼" to 2¼"). Surface: Smooth. Color: Bronzy. Strength: Stiff, erect, and slender.

Bloom:

*Size.*—Small. Average open size is 2 to 2¼ inches.

*Borne.*—Singly and several together in rounded clusters of three to five flowers.

*Stems.*—Short (8–10") and strong.

*Form.*—When first open: High centered. Permanence: Outer petals curl back with some quilling.

*Petalage.*—Number of petals under normal conditions: 20.

*Color.*—The upper sides of the petals are Red group 49B. The reverse sides of the petals are Red group 49B. The base of each petal has a small (⅛"×⅛"), Yellow group 8B half-moon at the point of attachment. The major color on the upper side is Red Group 49B.

*Variegations.*—None.

*Discoloration.*—At the end of the first day: No change. At the end of the third day: No change. By day five, the flower has faded to Red group 49C and then on day six to Red group 49D. By day seven, the petals drop cleanly.

*Fragrance.*—Slight.

Petals:

*Texture.*—Thick.

*Shape.*—Round.

*Form.*—Tips slightly recurved, edges slightly quilled.

*Arrangement.*—Imbricated. Petaloids in the center are few.

*Persistence.*—Drop off cleanly.

*Lastingness.*—On the plant: Long (six days). As a cut flower: Long (eight days).

Reproductive parts:

*Anthers.*—Size: Medium. Quantity: Many. Color: Yellow. Arrangement: Rectangular around styles.

*Filaments.*—Color: Reddish-brown.

*Pollen.*—Color: Gold yellow.

*Styles.*—Color: Greenish-white.

*Stigmas.*—Color: Greenish-white.

Plant:

*Form.*—Bush.

*Growth.*—Vigorous; dwarf; upright; branching; Height after one full season of growth in Somis, Calif. is 24" tall by 18" wide.

Foliage:

*Number of leaflets on normal mid-stem leaves.*—Five or seven.

*Size.*—Small (2¾"×1¾").

*Quantity.*—Abundant.

*Color.*—New foliage: Upper and Lower Surfaces: Greyed-purple 187A; Quickly turns green. Old foliage: Upper surface: Green group 136A. Lower surface: Green group 139C.

*Shape.*—Pointed oval.

*Texture.*—Upper side: Leathery.

*Edge.*—Serrated.

*Serration.*—Single, small.

*Petiole rachis.*—Color: Reddish.

*Petiole underside.*—Smooth with occasional prickles.

*Stipules.*—Medium to short (⅓" long); serrated, bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Short (⅛"); straight to hooked slightly downward.

*Color when young.*—Red.

Small prickles:

*Quantity.*—On main stalks: None. On laterals: None.

I Claim:

1. A new and distinct variety of rose plant of the miniature class, substantially as herein shown and described, characterized particularly as to novelty by its compact, upright, well-branched growth habit; resistance to rust and powdery mildew infection; very glossy, small, dark green foliage; and very attractive, well-formed, small, pure pink flowers.

* * * * *

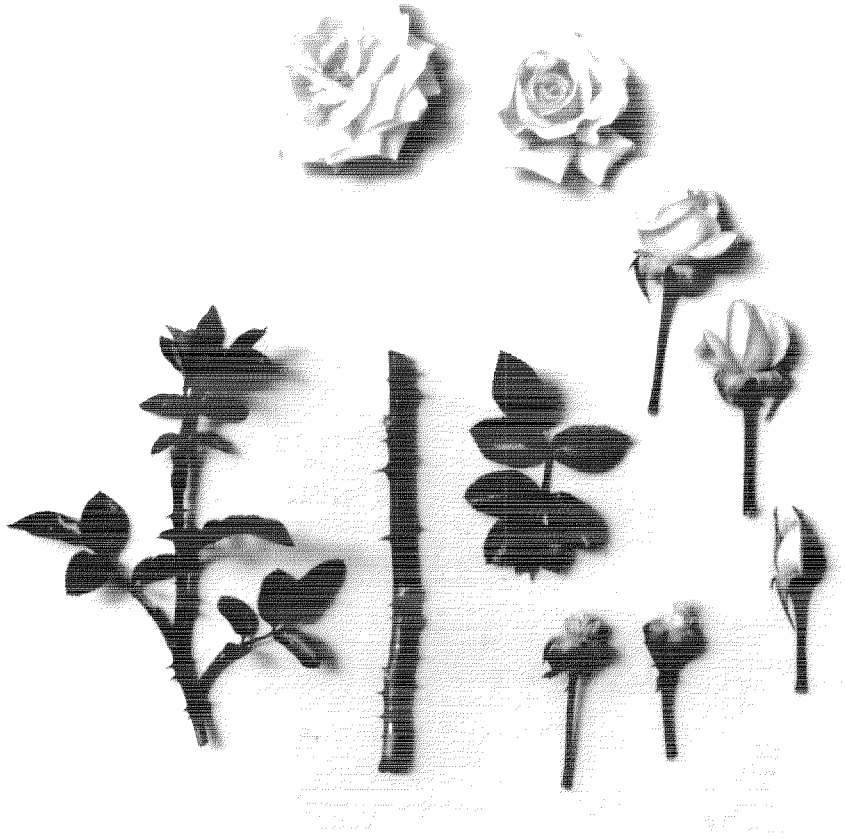
JACpoly

UNITED STATES PATENT AND TRADEMARK OFFICE

CERTIFICATE OF CORRECTION

PATENT NO. : PP10,929

DATED : June 1, 1999

INVENTOR(S) : Keith W. Zary

It is certified that error appears in the above-indentified patent and that said Letters Patent is hereby corrected as shown below:

Column 2, line 18, delete "(1 ¼" to 2 ¼")" and insert therefor --(1 ¼" to 1 ½")--.

Signed and Sealed this

Twenty-third Day of November, 1999

*Attest:*

Q. TODD DICKINSON

*Attesting Officer*

*Acting Commissioner of Patents and Trademarks*